United States Patent [19]
Meo, III

[11] Patent Number: 5,229,071
[45] Date of Patent: Jul. 20, 1993

[54] CATALYTIC OXIDIZER FOR TREATING FIXED QUANTITIES OF GASES

[76] Inventor: Dominic Meo, III, 1807 Tradewinds La., Newport Beach, Calif. 92660

[21] Appl. No.: 766,659

[22] Filed: Sep. 26, 1991

Related U.S. Application Data

[63] Continuation-in-part of Ser. No. 498,986, Mar. 26, 1990, abandoned, which is a continuation-in-part of Ser. No. 234,158, Aug. 19, 1988, abandoned.

[51] Int. Cl.$^5$ .................. A61L 2/00; A61L 9/00
[52] U.S. Cl. .................. 422/2; 422/30; 422/34; 422/126; 422/175; 422/181; 422/206; 422/187; 423/245.3
[58] Field of Search .......... 422/30, 34, 2, 126, 422/175, 181, 206, 187; 423/245.3, 213.2, 213.5

[56] References Cited

U.S. PATENT DOCUMENTS

| | | | |
|---|---|---|---|
| 3,598,543 | 8/1971 | Crosby et al. | 23/288 |
| 3,851,043 | 11/1974 | Gunther | 423/245 |
| 3,874,854 | 4/1975 | Hunter | 23/288 F |
| 4,410,492 | 10/1983 | Kaye | 422/27 |
| 4,702,892 | 10/1987 | Betz | 422/171 |
| 4,741,690 | 5/1988 | Heed | 431/7 |
| 4,770,857 | 9/1988 | Ludwig | 422/111 |
| 4,997,632 | 3/1991 | Rodewald | 423/240 |
| 5,128,101 | 7/1992 | Boynton | 422/31 |

FOREIGN PATENT DOCUMENTS 012286  8/1980  Japan .

OTHER PUBLICATIONS

Abstract of Japanese Patent No. 033418.
"Donaldson ETO-Abator System", Donaldson Company, Inc., Product Bulletin PB-ETO-001, 1988.
"Donaldson 125 CM ETO ABATOR", data sheets, Donaldson Company, Inc.
"ETO Abator-125 CFM, Outline", Donaldson Drawing No. 626P0038, dated Aug. 11, 1988, Donaldson Company, Inc.
"ETO Abator, 125 CFM", Donaldson Drawing No. 6261A2836, dated Jun. 7, 1988, Donaldson Company, Inc.

Primary Examiner—Jill A. Johnston
Assistant Examiner—N. Bhat
Attorney, Agent, or Firm—Hawes & Fischer

[57] ABSTRACT

A batch method and apparatus provides controlled release of gaseous air contaminants into the atmosphere through catalytic oxidation while minimizing both the energy required and the volume of waste gas exhausted into the atmosphere. The device has a recirculating gas stream driven by a recirculation fan which moves gas, normally and naturally present at start-up, through a bed of granular catalyst, in an oxidizer and into contact with the surface of a process-gas heater and back to the recirculation fan. The gaseous contaminants may be drawn into this system using a vacuum pump. Control of catalyst temperature is achieved based upon the novel system configuration, and without the introduction of dilution air, and the contaminant gas is introduced without controlling either flow rate or temperature.

21 Claims, 2 Drawing Sheets

CATALYTIC OXIDIZER FOR TREATING FIXED QUANTITIES OF GASES

The application is a continuation-in-part of U.S. patent application Ser. No. 498,986 filed Mar. 3, 1990, which was a continuation-in-part of U.S. patent application Ser. No. 234,158 filed on Aug. 19, 1988; both applications are now abandoned.

BACKGROUND OF THE INVENTION

1. Field of the Invention

This invention relates to a catalytic oxidation chamber and method of its use, particularly in minimizing energy consumption and the volume of waste exhaust, while treating a wide range of concentrations of air pollutants from both batch and continuous processes. The method and device of the present invention is particularly well suited to control of ethylene-oxide emissions from a gas sterilizer.

2. Brief Statement of the Prior Art

Catalytic oxidizers are commonly used in controlling atmospheric emissions. These oxidizers employ a catalyst within an oxidation chamber, which is typically filled with a granulated metallic oxide or a mixture of oxides, or an inert substrate such as alumina, over which a precious metal such as silver or platinum has been deposited. Regardless of which catalyst is used, proper operation of the oxidation chamber is critical. The constituent to be oxidized is typically referred to as a contaminant after it has been used for its central purpose. These contaminants are typically one or more combustible gasses. Most importantly, the total concentration of gaseous contaminants, hereafter combustible gasses, in the process airstream to be oxidized must not exceed a limit which is determined by the nature of the catalyst. This limit is generally set at 15 percent of what is referred to as the lower explosive limit, or L.E.L. When this lower explosive limit is exceeded, the heat of oxidation accumulates to excess, and the catalyst bed can overheat, unless special provisions have been taken to absorb this heat.

The most common method of preventing overheating of the catalyst bed is to add uncontaminated atmospheric "dilution air" to the process airstream entering the oxidation chamber, to lower the lower explosive limit and adsorb a portion of the heat released in the catalyst bed during oxidation. One Japanese Patent, No. 12286 to K. K. Zeon demonstrates this practice. The dilution-air stream is even identified as such in the patent abstract. Another method of preventing overheating in the catalyst bed is to place an inert solid material within the bed to absorb a portion of the heat released during oxidation.

To date, it has not been economically feasible or even desirable to use heat-absorbing material as the sole means of preventing overheating of the catalyst bed, using no atmospheric dilution air at all, due to the continuous nature of most processes and the enormous quantities of heat to be absorbed.

The use of heat-absorbing materials in oxidizes is generally limited to use in regenerative heat-recovery exchangers, which work by reversing the direction of air flowing through them. Examples include U.S. Pat. No. 4,702,892 to Erwin C. Betz, entitled "Heat Recuperative Catalytic Oxidation Device", and U.S. Pat. No. 4,770,857 to Gerhard Ludwig, entitled "Process and Apparatus for the Catalytic Reaction of Gasses".

A less frequent use of heat-absorbing materials includes the retention of the heat of oxidation to slow the cooling of the catalyst bed, when the process air flow and supply of oxidizable combustible gasses stops. Examples include U.S. Pat. No. 3,598,543 to Howard M. Crosby, entitled "Catalytic Exhaust Purifier", and U.S. Pat. No. 3,874,854 to Joseph E. Hunter, entitled "Catalytic Converter".

In addition to limiting the maximum concentration of oxidizable contaminants in the process airstream entering the oxidation chamber, a second critical operating variable is residence time, or the time it takes for the process air stream to pass through the catalyst bed. This is achieved by using the proper combination of process air flow rate and depth of catalyst bed. A third critical operating parameter is the operating temperature of the catalyst bed. It must be greater than the minimum temperature needed to obtain the desired degree of oxidation or control efficiency, yet it must be lower than the temperature at which the catalyst is damaged. Traditionally, the temperature of the catalyst bed is generally controlled by using the proper ratio of dilution air which has the effect of cooling both the bed and dissipating any heat available from a process air heater employed to heat the bed.

Optimum performance of an oxidizer is obtained when the optimum combination of residence time and catalyst bed temperature, is achieved for a given concentration of oxidizable contaminant in the process airstream. In practice, this optimum combination, known as the time-temperature relationship is very difficult to achieve. When an oxidizer, including its oxidation chamber is put into service, any change in process air flow rate or concentration of oxidizable contaminant upsets the time-temperature relationship. The present state of the art requires control of the temperature of the oxidation chamber, especially in response to changes in process air flow rate or contaminant concentration, so that the desired degree of emission control or oxidation efficiency is achieved, even at the expense of wasted energy.

Changes in residence time in the catalyst bed are generally not possible, as the depth of the catalyst bed is fixed, and the process air flow rate cannot be easily changed without creating problems in the process from which the air is flowing. Often, the only variable which can be controlled is the process air temperature, even when this does not achieve optimum results.

One disadvantage to using catalysts to enhance oxidation of combustible gases is the susceptibility of the catalyst to poisoning and masking. Poisoning is the reaction of a contaminant with the catalyst itself. Masking is the deposition of a contaminant onto the surface of the catalyst, blocking the availability of reactive sites at the surface. Both phenomena reduce the effective active surface area of the catalyst and make it less active, or effective. The current state-of-the-art methods utilized in catalytic oxidation control both poisoning and masking by preventing a gaseous contaminant, capable of causing either effect, from entering the process air stream entering the oxidation chamber.

In the event either poisoning or masking occurs, the catalyst will lose activity and it must be removed. The catalyst is either reinstalled after cleaning, or replaced with new catalyst, to restore the efficiency of the oxidizer.

Catalytic oxidizers have been used for many years, and at various types of facilities, as air-pollution control devices. A typical control efficiency set by regulatory agencies for the control of smog-forming chemicals is 95 percent. Recently, regulatory agencies have adopted standards for the control of toxic air emissions which are known or are suspected of causing cancer. These regulations are much stricter than those used to control smog-forming chemicals, requiring up to 99.99 percent control of emissions passing through the oxidizer, and they require that the total mass of emissions released be limited to a designated amount.

The mass or weight of emissions released from an oxidizer is calculated by simply multiplying the exhaust gas flow rate times the concentration of gas contaminant in the exhaust. As the practical limit on reducing the concentration of gas contaminant in the exhaust is reached, the only way to lower the weight of emissions released into the atmosphere, is to lower the total exhaust gas flow rate. Because the regulations for controlling air toxics are relatively new, little work has been performed in minimizing exhaust flow rate. The oxidizer presented here is designed specifically to minimize exhaust gas flow rate.

It is difficult to design a catalytic oxidizer specifically for controlling the emissions from a batch process. Often, both the flow and concentration of combustible gasses vary during the operating period of the process. When cooling of the catalyst bed is achieved through dilution air, the flow of dilution air must be continuously adjusted, for optimum operation. This is difficult and expensive to accomplish and is therefore generally not practiced.

As an example of this difficulty, existing Catalytic oxidizers are not well suited to controlling emissions from gas sterilizers, which operate as a batch process. Gas sterilizers use a toxic sterilizing gas which contacts the objects to be sterilized. After sterilization, the toxic sterilizing gas must be safely removed, reacted to eliminate its toxicity, and vented. Catalytic oxidizers currently used to control emissions from gas sterilizers operate with fixed dilution-air flow rates, selected to keep the oxidation chamber small and inexpensive. The small-sized oxidation chamber and fixed dilution-air flow therefore limits oxidation capacity. This limited capacity of the oxidizer retards the normal rate of venting of the gas sterilizer and lengthens the total time required to operate the gas sterilizer.

In the case where exhaust gases are recirculated to conserve energy in catalytic oxidation, the reacted exhaust gases are typically mixed back into the gaseous contaminant to be oxidized. This mixture is then passed through the catalyst bed. The state-of-the-art method currently used for mixing the exhaust gas with the incoming gaseous contaminant is to use an empty chamber or section of ductwork for the mixing. The degree of mixing is limited by the lack of turbulence in these mixing schemes, and the mixture is not truly homogeneous and uniform. As a result, the intensity of the oxidation process, which is dependent upon the concentration of oxidizable contaminant, varies across the surface of the catalyst bed. The temperature of the catalyst is not uniform, and optimum efficiency of the bed is not achieved.

The state of the art used to overcome this less-than-optimum catalyst efficiency is to use more catalyst, or to operate the bed at a higher temperature. Either approach is wasteful and increases the operating cost of the oxidizer.

Specifically, sterilizers are commonly used in hospital and food applications. These sterilizers have a chamber which is sealed and filled with a sterilant gas mixture containing from 10 to 100 weight percent ethylene oxide. Commonly, the ethylene oxide is diluted with an inert gas such as one of the various chlorofluorocarbons, e.g., Freon 12, or carbon dioxide, to create a nonflammable gas mixture.

In practice, the objects to be sterilized are placed in the chamber, the chamber is sealed and filled with the sterilant gas for a sufficient time to permit penetration of the ethylene oxide throughout the objects and effect complete sterilization. Once the sterilizing has been completed, the sterilant gas is pumped from the sterilizing chamber by a vacuum pump. When the exhaust from the vacuum pump is vented to the atmosphere, it contributes significantly to air pollution, as ethylene oxide is a very toxic gas which is known to cause cancer and is objectionable in the environment. In some areas of the country, notably Southern California, regulations prohibit direct venting of ethylene oxide to the atmosphere. In such areas, ethylene oxide emissions must be controlled. This can be accomplished by passing the sterilant gas mixture containing ethylene oxide mixed with air over an oxidation catalyst at temperatures sufficient to oxidize ethylene oxide to carbon dioxide and water vapor.

All the catalytic oxidation systems which have been employed previously to control ethylene oxide emissions mix the ethylene oxide with a constant flow of air, thereby controlling the temperature of the catalyst bed. The air added to the ethylene oxide is a heat sink for the heat of oxidation of the ethylene oxide. The more concentrated the ethylene-oxide emission, the more air must be added to control the temperature rise in the catalyst bed, to prevent overheating and thermal damage to the catalyst, and to prevent thermal breakdown of the chlorofluorocarbon, should it be present as a diluent gas.

The existing catalytic oxidation systems are not ideally suited for the oxidation of a fixed quantity of ethylene oxide such as is encountered in venting of sterilizing chambers. As the sterilizing chamber is vented and fresh air is subsequently washed into and through the sterilizing chamber to remove residual ethylene oxide, the concentration of ethylene oxide in the air stream entering the catalytic oxidizer continuously declines. Consequently, the catalyst is never provided with a gas mixture having a constant concentration of ethylene oxide. This results in serious compromises in the design of the oxidizer which is designed to treat a relatively large volume of air, dictated by the initial high concentration of ethylene oxide vented from the sterilizing chamber. Except for the beginning of the venting of the sterilizing chamber, existing catalytic oxidizers are oversized and are very inefficient in their use of energy. Even with the attachment of heat recovery devices, the inefficiency of heating relatively large volumes of air to treat decreasing concentrations of ethylene oxide cannot be overcome.

BRIEF DESCRIPTION OF THE INVENTION

This invention provides a means for controlling the release of gaseous air contaminants into the atmosphere through catalytic oxidation. It does this while minimizing both the energy required and the volume of waste gas exhausted into the atmosphere. The design will work on both continuous and batch processes, but it is particularly effective for batch processes.

In principle, the oxidizer has a recirculating air stream driven by a recirculation fan which moves air, normally naturally present at start-up, through a bed of granular catalyst, and into contact with the surface of a process air heater and back to the recirculation fan. At start-up, the temperature of the catalyst bed is controlled by controlling the temperature of the recirculating air which is controlled by regulating the temperature of the process heater.

Combustible gasses produced by a commercial process, apart from and external to the oxidation chamber, are introduced into the recirculating air stream of the oxidizer, on the suction side of the fan. These combustible gasses instantly mix with and are both diluted and heated by the recirculating air stream.

The diluted and heated combustible gasses are drawn through an in-line mixing element which further mixes the diluted combustible gasses. Then, the gaseous contaminates are drawn through the recirculation fan and are forced through the catalyst bed, where they are oxidized to form carbon dioxide and water vapor.

The recirculating air contains oxygen which is consumed in the oxidation reactions which occur on the surface of the granular catalyst. Should these oxidation reactions consume oxygen in such quantities that additional oxygen in the recirculating air stream is needed to maintain catalytic performance, filtered air from the surrounding atmosphere, called "oxidation air", is admitted into the recirculating air stream on the suction side of the fan, upstream of the in-line mixing element.

The oxidation reactions which occur on the surface of the granular catalyst produce heat. As discussed above, there are two demonstrated approaches to controlling this heat and preventing over heating of the catalyst. They are air dilution and heat-absorbing solids. When the oxidizer of the instant invention is used to control the gaseous emissions from a batch process, the total heat produced by the oxidation reactions is known, and a known quantity of sufficient catalyst can be provided to be used to absorb all of this heat without interrupting the operation of the process. Therefore, in the inventive method, no externally-obtained dilution air is required to absorb heat and prevent the over heating of the catalyst. If it is necessary to introduce air during oxidation, it is only for the purpose of supplying oxygen for the oxidation process, and the amount of oxidation air introduced is limited to the amount needed for oxidation.

The above-described method of oxidation of combustible gasses from batch processes has the important advantage of minimizing the volume of waste gas exhausted into the atmosphere. With the device and method of the instant invention, the flow of exhaust gas, namely the oxidation products and associated air, cannot exceed the combination of the combustible gas, gasses present with the combustible gas, and the oxidation-air flow into the oxidation chamber. Because no dilution air is required to prevent overheating of the catalyst bed, and the oxidation-air flow is relatively small, the exhaust gas flow is consequently minimized.

Ethylene oxide has been identified by Federal and State regulators as an air toxic species. Sterilizers predominantly found in hospitals and other medical facilities utilize ethylene oxide as a sterilizing gas. In the various hospitals and medical facilities, the minimization of the exhaust gas flow rate is a significant goal when controlling air toxics. Because this invention minimizes the exhaust gas flow rate, it has an advantage over other oxidizers which do not minimize the exhaust gas flow rate in controlling ethylene-oxide emissions.

Another advantage of the device and method of the present invention in controlling combustible gases from gas sterilizes is the ease with which the invention can respond to the changing concentration of the combustible gases pumped out of the gas sterilizer, after sterilization is complete.

These combustible gases are most concentrated when the vacuum pump first begins to remove ethylene oxide or some other gas sterilant from the gas sterilizer. They are least concentrated when the vacuum pump completes evacuating the sterilizer. The connecting piping between the gas sterilizer and the invention is arranged such that the combustible gases pumped by the vacuum pump are introduced into the recirculating gas stream at a point before the recirculating gas stream enters the catalyst bed.

The maximum concentration of the combustible gas required for its safe introduction into the catalyst bed, without overheating the catalyst must be insured irrespective of the concentration at which it is made available. This invention uses the velocity of the recirculation-air stream only to reduce the concentration of the combustible gas entering the oxidizer. No external dilution air is required. The reduction in the concentration of the combustible gas is therefore achieved by simply adjusting the speed of the recirculation fan. High fan speeds produce high recirculation rates and large reductions in concentration of the combustible gas, while low fan speeds achieve small reductions in concentration of the combustible gas.

As described above, when the combustible gas is provided through evacuation of a sterilization chamber, a high flow rate of combustible gas will initially occur, followed by a declining flow rate of combustible gas. Given this operating parameter, and using the above control logic, the fan speed is high at the beginning of the oxidation process, and reduced in speed during and near the end of processing.

As the air, whether initially present with the catalyst, or associated with the combustible gas entering the oxidizer, recirculates through the recirculation duct work and catalyst bed in the oxidizer, it heats up due to frictional resistance. This frictional heat assists in keeping the temperature of the catalyst above the minimum needed for efficient oxidation. The greater the air recirculation rate, the less heat is needed from the process heater. For this reason, there is no energy penalty for increasing the speed of the recirculation fan, to permit a higher flow of combustible gas from the gas sterilizer into the oxidizer. Consequently, there is no reason to retard the rate at which combustible gas enters the oxidizer from the sterilizer, as is required for oxidizers which use dilution air at fixed air dilution flow rates that must be kept low to minimize energy consumption.

The gas emissions from a gas sterilizer often contain a chlorofluorocarbon which is not oxidized on the surface of the catalyst. With regard to the oxidizer, the fluorocarbon is problematic in that it simply adsorbs onto the surface. When this occurs, the catalyst becomes less effective, in proportion to the amount of chlorofluorocarbon absorbed. This phenomenon is referred to as "masking" and can be quite serious.

The device and method of the instant invention is designed to respond to chlorofluorocarbon masking. A special air-purge cycle is used to admit large quantities of atmospheric air into the oxidizer. This air purge strips the chlorofluorocarbon off the surface of the catalyst and restores its activity.

For a given combustible gas, there is an optimum time-temperature relationship for catalytic oxidation, as discussed earlier. It is normally difficult to independently control both temperature and residence time in oxidizers which rely on dilution air to limit the temperature of the catalyst bed. When conventional oxidizers are used, the change in the dilution air flow in response to a change in the temperature of the catalyst bed changes the total air flow through the oxidizer, thus changing the time it takes for the air to pass through the catalyst bed, known as the residence time.

When this invention is used to process combustible gas from batch processes, the residence time and catalyst bed temperature can be independently controlled. For a given, usually very small oxidation air flow rate, the speed of the fan can be adjusted to control the residence time of the recirculating air stream in the catalyst bed. The temperature of the process heater can be used to independently control the temperature of the catalyst bed by regulating the temperature of the recirculating air stream. With the above control flexibility, the time-temperature relationship can be adjusted for optimum oxidizer operation.

For example, at the beginning of the sterilizer venting cycle, when the vacuum pump starts and the concentration of combustible gas from the gas sterilizer is high, a short residence time within the catalyst section of the oxidizer will achieve a high degree of control efficiency. Near the end of the venting cycle, when the emissions are dilute, a longer residence time is necessary. Changing the speed of the fan during the processing cycle, will effect the desired change in residence time. Simultaneously, any desired changes in the temperature of the catalyst bed can be made independently by adjusting the temperature of the process heater, without effecting the volumetric flow rate of the recirculating air stream which controls the residence time in the bed.

The inventive method and device herein provides a much more efficient method for mixing the exhaust gas with the incoming combustible gas to be oxidized, than exists in state-of-the-art catalytic oxidizers. Immediately downstream from the point at which the combustible gas is injected into the recirculating airstream, a highly efficient in-line mixing element, designed specifically to mix two gas streams is located. This in-line mixing element results in a very uniform gas mixture entering the catalyst bed. This results in a catalyst temperature which is more uniform, and a catalytic efficiency which is higher.

There is a pressure drop in the recycle stream as it flows through the mixing element, for supplying the energy needed to mix the two gas streams. The frictional resistance provided by the mixing element causes a slight rise in the temperature of the air. As discussed previously, heat generated in this manner has the beneficial effect of reducing the load on the process heater used to heat the recirculating air stream. The energy needed to operate the in-line mixer is used to keep the catalyst bed warm and reduces the cost of operating the process heater while it improves the operating efficiency of the catalyst bed.

This invention more specifically relates to a system and method for catalytic oxidation of a gas or gas mixtures used in batch processes such as gas sterilization. In the case of gas sterilization where a known quantity of combustible gas is used, an oxidizer vessel is provided which has sufficient gas volume and a sufficient quantity of solid catalyst to permit efficient processing of all of the sterilant gas without interrupting the operation of the sterilizer prior to the end of its normal operating cycle. In the method and device of the present invention, the oxidizer is preheated to catalytic initiation temperature, typically 300 degrees Fahrenheit, by recycling the air, normally present within the oxidizer during start-up, or associated with the catalyst bed during time periods when the oxidizer is not in use. This preheating is performed by circulating the air normally present through a pre-heater, and over the catalyst to preheat the solid catalyst.

The sterilizer chamber, after sterilization has occurred, is evacuated using a vacuum pump at a rate, which is from about 1.1 to about 1.7 percent of the gas-recycle rate. The evacuated, combustible ethylene-oxide gas is pumped into the oxidizer by the pumping action of the vacuum pump. The resultant mixture of evacuated gas, and the recycle air, which was normally present at start-up, is passed over the catalyst. The exothermic heat release from oxidation of the ethylene oxide is absorbed by the solid catalyst and the recirculating gas, the recirculating gas being increasingly filled with oxidation products.

As the exothermic oxidation proceeds, the preheat step becomes unnecessary and is discontinued. The quantity of sold catalyst contained within the oxidizer is preselected to provide a sufficient heat sink to absorb all of the heat of oxidation of the amount of ethylene oxide contained within the sterilizer chamber, thereby preventing the temperature within the oxidation zone from rising to excessive magnitudes, which could cause damage to the catalyst or cause thermal decomposition of the chlorofluorocarbon, should it be present as a diluent gas.

The sterilizer chamber is evacuated with a vacuum pump that supplies the ethylene oxide sterilant gas to the oxidizer. Once the chamber has been evacuated, the sterilizer chamber may be washed with air by placing the interior of the sterilizer, which is at sub atmospheric pressure, in communication with the atmosphere to introduce air into the chamber. The sterilization chamber is then resealed and again evacuated with a vacuum pump and the evacuated gas, containing the wash air, is passed to the oxidizer. The air washing is repeated as many times as is necessary to ensure essentially complete removal of the sterilant gas from the sterilization chamber.

When the temperature of the catalyst declines to a magnitude at or near the initiation temperature during the air washing process, the pre-heater can be reactivated and heat can be supplied to the recycle gas to maintain the temperature above the initiation temperature for oxidation of any further ethylene oxide which may be present during the air wash cycles.

This invention eliminates the need for adding air to the ethylene oxide vented from the sterilizer, to absorb the heat of oxidation of the ethylene oxide and prevent overheating of the catalyst bed, or the thermal decomposition of the chlorofluorocarbon, should it be present. Instead, the catalyst bed itself is used to absorb most of the heat of oxidation of the ethylene oxide. The use of the catalyst bed in this manner eliminates the need for a heat-recovery device to transfer heat from the hot exhaust stream to the cool incoming air stream. The oxidizer of the instant invention operates very efficiently, over the entire range of concentrations of ethylene oxide in the air stream entering the oxidizer during the venting and air-washing of the sterilizer. The oxidizer described in this invention is the first oxidizer designed specifically for batch processes. The batch aspect of this invention involves the processing of a finite volume of combustible gas. The finite volume of combustible gas enables a catalyst volume to be employed wherein most of the heat of oxidation of the gas is absorbed by the catalyst bed, especially during the early portion of the oxidation process, and then released, especially during the later portion of the catalyst process, to provide the optimum use of energy and catalyst efficiency.

BRIEF DESCRIPTION OF THE DRAWINGS

The invention will be described with reference to the drawings of which.

DESCRIPTION OF PREFERRED EMBODIMENT

Figure 1:
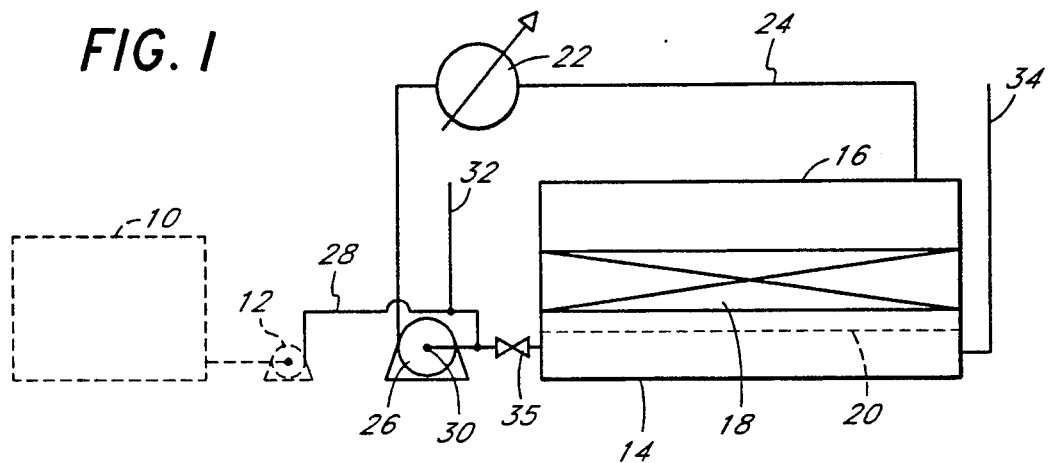
FIG. 1 illustrates a flow diagram for the oxidation of the invention.

Referring to FIG. 1, the method for oxidation of the ethylene oxide contained within a sterilizer chamber 10 will be described. The sterilizer chamber 10 has a constant volume and is provided with a sterilant gas that typically contains from 10 to 100 weight percent ethylene oxide. Commonly, the ethylene oxide is reduced in concentration with an inert gas such as one of the various chlorofluorocarbons, as for example, Freon 12, or carbon dioxide. The sterilizer is a commonly used item in hospitals, pharmaceutical firms, and food processing plants to sterilize hospital supplies, pharmaceutical products and foods by introducing the material to be sterilized into the chamber, closing the chamber door, evacuating the chamber and then supplying the chamber with the sterilant gas.

Referring to FIGS. 1-4, the sterilizing chamber 10 and vacuum pump 12 are shown in phantom lines to represent a typical, often preexisting installation.

The oxidizer 14 of this invention is shown in solid lines and includes an oxidizer vessel, or housing 16 which contains a predetermined quantity of a solid catalyst 18. The catalyst is contained as a fixed bed, supported on a foraminous plate 20 which is adapted for through flow of a gas mixture. The oxidizer vessel, or housing 16 also has a predetermined gas volume, and has a recycle duct 24 for recycling of the gas through a pre-heater 22 and back to the oxidizer housing 16 using a recycle gas blower 26. The discharge 28 of the vacuum pump 12 of the sterilizer 10 is connected into the recycle duct 24, upstream of the suction 30 of the recycle gas blower 26. A line 32 is provided for introduction of air, also upstream of the suction 30 of the recycle gas blower 26. The oxidizer system 10 has a line 34, in the shape of a round conduit, to exhaust a controlled flow of gas from the oxidizer vessel, or housing 16. A valve 35 is positioned between the oxidizer vessel or housing 16 and the recycle as blower 26.

The method of the invention is practiced by recycling of the gas volume within the oxidizer vessel, or housing 16 over the preheater 22 wile supplying sufficient heat to the preheater 22 to raise the temperature of the recycle gas, and the catalyst to the initiation temperature for oxidation of ethylene oxide. Typically this temperature is about 300 degrees.Fahrenheit, and this is the preheat temperature desirable in the method. When the catalyst reaches the initiation temperature, the sterilizer chamber 10 can be evacuated by starting the vacuum pump 12 and pumping the contents of the sterilizer chamber 10 into the recycle gas stream. In a typical application, the vacuum pump 12 and the recycle gas blower 26 of the oxidizer 14 are sized so that the percent of evacuated gas from the sterilizer chamber will be from one to about ten percent of the recycle stream.

When the resulting gas mixture is introduced into the oxidizer, oxidation will occur and exothermic heat of oxidation will be released, further contributing to the temperature increase of the solid catalyst. When the catalyst temperature, as measured by the recycle-gas temperature, exceeds a predetermined value, which can be determined by temperature probes within the catalyst bed, the preheater 22 is deactivated and the catalyst 18 will continue to heat from the exothermic heat release, alone. The mass of catalyst which is used in the oxidation zone is selected to provide a sufficient heat sink which permits the entire contents of the sterilizer chamber 10 to be oxidized over the catalyst without reaching the decomposition temperature of the chlorofluorocarbon in the gas mixture, which is about 900° to 1000° F., should it be present. The maximum design temperature is approximately 600 degrees F. Preferably, the temperature of the catalyst is maintained at or below 550 degrees F. by providing a sufficient mass of solid catalyst within the oxidation zone.

In a typical application, the sterilizer chamber will be evacuated in approximately 20 minutes. After substantial complete evacuation, the sterilizer chamber 10 is vented to the atmosphere to air wash the chamber 10 of any residual amounts of ethylene oxide. This is accomplished by venting the chamber through an air inlet valve 36 to introduce air at atmospheric pressure, closing the inlet valve 36 and then resuming evacuation of the chamber with the vacuum pump 12. This process of filling the sterilizer chamber 10 with air, evacuating the chamber and passing the evacuated contents over the catalyst in the oxidizer 10 of the invention is practiced as many times as is necessary to remove essentially all of the ethylene oxide. During this air washing, it will be observed that the catalyst will cool as the concentration of ethylene oxide in the inlet air mixture is insufficient to maintain the temperature. In a typical application, the catalyst will cool to at or near the minimum initiation temperature of 300 degrees F. within approximately 100 minutes using a constant gas recycle rate. As each venting of the sterilizer chamber requires approximately 20 minutes, the catalyst will retain sufficient heat to permit approximately five air washes without requiring that heat be supplied from external sources.

When the chamber 10 is washed with air more than five times, the preheater 22 can be activated and heat can be added as necessary to maintain the catalyst temperature at or above the initiation temperature of 300 degrees F. Further, valve 35 can be closed in order to utilize recycle fan 26 to pull wash air once through the oxidizer housing 16. Slight adjustments of valve 35 will enable the recycle to be more finely controlled on a scale between complete recycle and no recycle.

EXAMPLE

A typical calculation for the amount of catalyst needed to absorb the heat of the oxidizing ethylene oxide is as follows. First, a basis of one pound of ethylene oxide gas is set upon which the calculations are to be based. The result may be adjusted proportionately for amounts of ethylene oxide gas less or greater than the one pound basis by ratio multiplication.

The heat liberated by the oxidation of one pound of ethylene oxide is reported in the literature to be 12,760 BTU. The catalyst temperature can rise from about 300 degrees Fahrenheit to about 500 degrees Fahrenheit, representing an acceptable temperature range of about (500−300)=200 degrees Fahrenheit. The mass of the catalyst required is given by the relationship $Q = m\, c_p\, \Delta T$, where m is the mass of catalyst, $c_p$ is the heat capacity of the catalyst and $\Delta T$ is the permissible rise in temperature. In this example the catalyst used is HOPCALITE®. HOPCALITE® is a registered trademark of the Callery Chemical Company, a division of Mine Safety Appliances Company of Pittsburgh, Pa. HOPCALITE® has the formula $MnO_2$—CuO and is available in several types depending upon the moisture tolerance required. HOPCALITE® is commercially available as a granular solid having a density of from 0.75 to about 0.95 grams per cubic centimeter. This catalyst has a heat capacity of 0.28 BTU per pound degree Fahrenheit. The equation is rearranged to yield an expression for mass of catalyst as follows:

$$m = \frac{Q}{c_p \Delta T} = \frac{12{,}760 \text{ BTU}}{0.28 \text{ BTU/LB-}°\text{F.} \times 200°\text{ F.}} = \frac{227.9 \text{ Pounds of Catalyst}}{\text{Pound of ethylene oxide}}$$

This computation assumes that no heat is lost to the environment and that no appreciable heat will be absorbed by the gas stream in the oxidizer, either from the air present at start-up, combustible gas entering the oxidizer, or from the combustion products.

Next, the bed depth must be calculated. It is known from field data that for the HOPCALITE® catalyst, a residence time of 0.30 seconds is necessary to ensure complete oxidation of ethylene oxide. The most limited residence time occurs for the highest flow rate of recycle. To achieve a cost-effective pressure drop and good performance, the gas velocity entering the catalyst bed should vary from between about 30 feet per minute to about 50 feet per minute. Using an average of about 40 feet per minute, the bed depth, D, should be equal to the product of the velocity times the residence time, or D=Vt. Here D=0.67 feet/second×0.30 seconds=0.2 feet or about 2.4 inches.

The recirculation rate is calculated based upon the maximum concentration expected in the oxidizer. For ethylene oxide, the lower explosive limit is about three volume percent, 3% by volume, or about 30,000 parts per million. The concentration must be reduced to no more than fifteen percent (15%) of this limit, or about 4,500 parts per million. Most hospitals use a mixture of ethylene oxide and freon-12 wherein ethylene oxide is present in the mixture at about 27 volume percent, or 270,000 parts per million. The ratio of reduction in concentration is therefore 270,000 parts per million/4,500 parts per million, or a ratio of 60 to 1.

The flow rate from a vacuum pump 12 is initially about 10 cubic feet per minute, at the outset of pumping, and declining as a vacuum is created in the sterilization chamber 10. Since the ratio is 60 to 1, if 10 cubic feet per minute of gas is supplied, the recycle must be 60 times this volume rate, or 10 cubic feet per minute×60 (ratio)=600 cubic feet per minute, for the recycle necessary to reduce the concentration of the incoming ethylene oxide gas mixture. Since this design calculation is based on a maximum expected ethylene oxide content, it is desirable to design a system whose design will not be exceeded in the event that the concentration of the ethylene oxide the sterilizer has an unexpectedly high concentration. Increasing the recycle flow, or other design computations by up to 50% of their expected value would be a good rule of thumb to insure that the design limits are safe.

Referring now to FIGS. 1-4, the oxidizer 14 which is used in the invention will be described. The oxidizer 14 is mounted on a platform 38 that supports the oxidizer housing 16, the recycle gas blower 26 and the necessary ducting and piping. The catalyst is contained in a modular cell 40 (see FIG. 4) which has a chamber formed by end plates 42 and 44 with a surrounding outer, foraminous shell 46. The end plates have fill ports 43 which are closed with cover plates 41. The cell 40 has an inner shell 48 which is also foraminous, thereby permitting radial flow through the cell 40. The outer shell 46 and inner shell 48 are formed of perforated sheet metal. The cell design provides the area desired for the optimum flow velocity of the gas, about 25 to 35, preferably 30 feet per minute. The preferred cell design provides a bed depth of 3 inches to the flow of the gas mixture, thereby providing the desired residence time for complete oxidation of ethylene oxide. Other cell designs may be used, as desired.

The catalyst which is used in this treatment is a conventional granulated copper oxide-manganese dioxide catalyst. A preferred catalyst is HOPCALITE®, which is available from Callery Chemical Company, Division of Mine Safety Appliances Company. This catalyst has a grain size from 8 to 14 mesh and a surface area of about 200 square meters per gram (15,571 square feet per pound).

As previously mentioned, the amount of the catalyst which is employed is sufficient to absorb the exothermic heat release from the oxidation of the amount of ethylene oxide contained within the sterilizer chamber. Accordingly, the oxidizer is sized for the particular sterilizer chamber to be employed. In a typical hospital application, the gases sterilizer holds between 0.45 and 3.38 lbs. of ethylene oxide. At the rate of 228 pounds of catalyst per pound of ethylene oxide, 103 to 771 pounds of catalyst will be suitable for use with most conventionally sized hospital sterilizer chambers.

The gas, after passing through the catalyst cell 40 is collected in the outlet 50 which is mounted at one end of the oxidation housing 16. The outlet duct 52 is connected into the suction of the recycle gas blower 26 which discharges through a discharge duct 54 to the preheater 22 which includes an electrically heated coil 56 mounted directly in the duct. The return air duct 58 from the preheater 22 is connected to the catalytic oxidation housing 16 being directly mounted with external flanges 60 to the inlet end of this vessel.

The evacuated sterilant gas that is removed from the oxidizer vessel 10 by its vacuum pump 12 is connected into the outlet duct 52, where it is introduced on the suction side of the recycle gas blower 26 through a small inlet line 62. This insures that the gases are intimately mixed during passage through the recycle gas blower 26.

The oxidation vessel is also provided with an outlet conduit 34 which can exhaust directly into the atmosphere or into a suitable exhaust stack. This outlet provides exhaust gas flow that is equal to the introduction of gas into the oxidation system.

The oxidizer 16 is also provided with an air inlet 68 which contains a suitable filter 70, e.g., pleated paper, to remove any dust from the inlet air. This inlet air is passed through a flow control valve 72 to control its rate of introduction and into the outlet duct 52, preferably upstream of the recycle gas blower 26 so that the air is intimately mixed with the gas mixture during the passage through the recycle gas blower 26.

The catalyst cell can be suitably supported within the oxidation vessel on an internal wall 74 so that the cell 40 is received therein and can be removed simply by unbolting the cover plate 73 for access to the cell, and then removing the cell by pulling it from its support within the oxidation vessel. One or a plurality of these cells can be disposed within the oxidation vessel, depending upon the size and desired capacity of the oxidation vessel.

The following example will illustrate the invention and serve to demonstrate results obtainable thereby.

EXAMPLE

Figure 2:
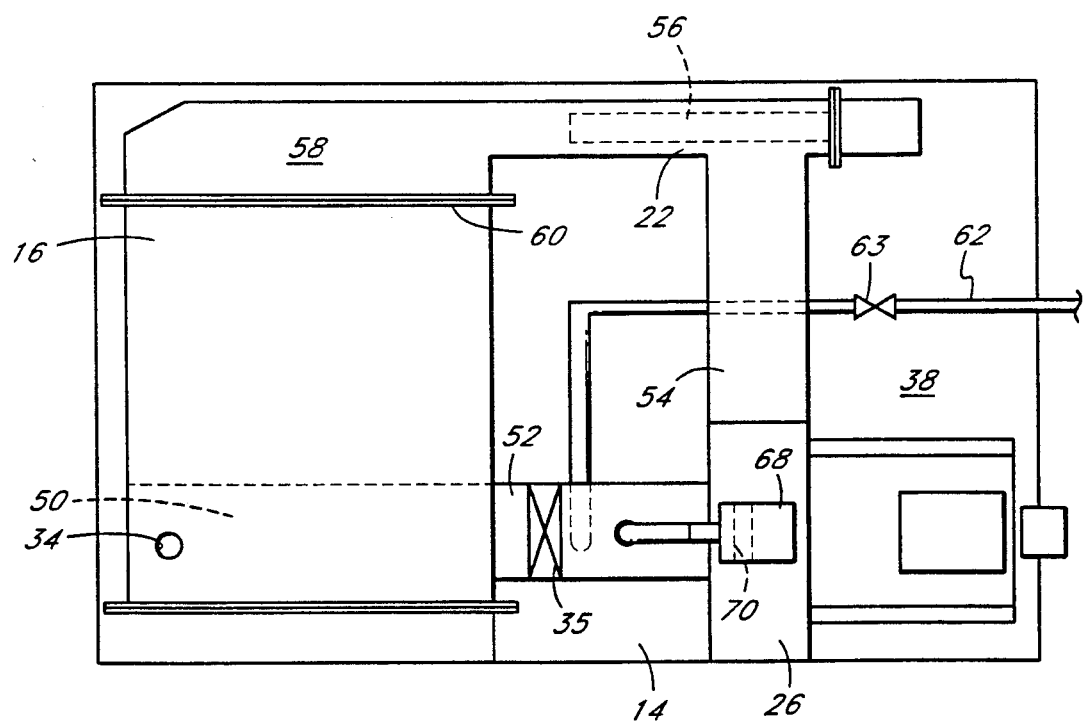
FIG. 2 is a plan view of a suitable oxidization apparatus.
Figure 3:
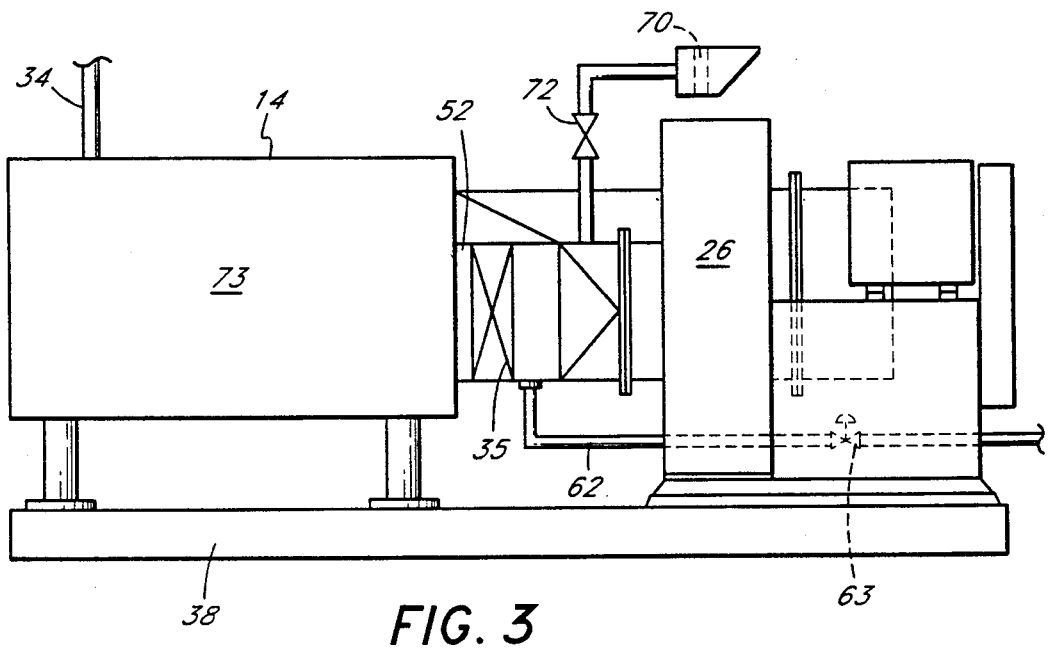
FIG. 3 is a side elevational view of the oxidation apparatus.
Figure 4:
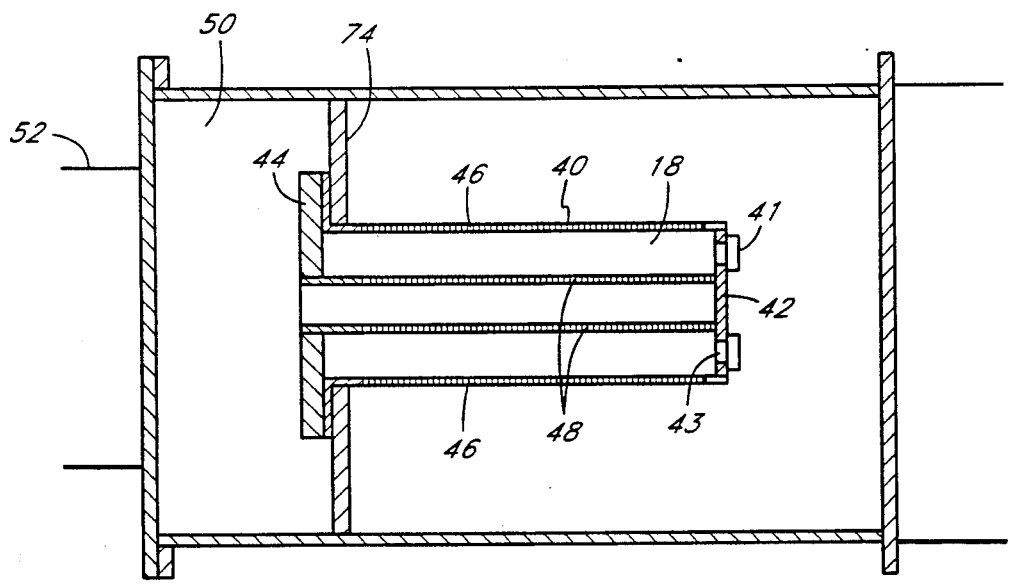
FIG. 4 is an elevational sectional view of the oxidation apparatus.

In this example, an oxidation vessel substantially of the shape shown in FIGS. 2 and 3 is loaded with a quantity of 100 pounds of catalyst contained within a single cell. This catalyst has a total surface area of 1.56 million square feet. The catalyst and catalytic oxidizer are used for the treatment of the ethylene oxide emissions from a small hospital sterilizer having a size of $20 \times 20 \times 38$ inches and an internal volume of 8.8 cubic feet. The sterilizer is supplied with a sterilant gas mixture containing 12 weight percent ethylene oxide in Freon 12 so that the total weight of ethylene oxide in the sterilizer which must be oxidized during venting is 0.41 pounds.

After the sterilizing vessel has been used to sterilize surgical instruments, the sterilizing chamber is evacuated with its vacuum pump. Prior to evacuation, the oxidizer is preheated to 300 degrees F. by recycling its internal gas volume over an electric coil preheater at a flow rate of 900 cubic feet per minute. When the catalyst bed reaches 300 degrees F., the vacuum pump of the sterilizer is started, and the sterilizing chamber is evacuated at a rate of 10 standard cubic feet per minute. The evacuated gas is discharged from the vacuum pump into the suction side of the gas blower of the oxidizer. When the oxidation process has generated sufficient heat, the electric heating coils of the preheater are disengaged. This evacuation is continued for a period of 20 minutes which is effective to evacuate the sterilizer chamber to a low vacuum pressure. The catalyst bed reaches a temperature of 450 degrees F. during this evacuation.

After the sterilizer chamber has been evacuated, its inlet valve is opened and air is flushed into the sterilizer chamber. When the sterilizer chamber reaches atmospheric pressure, the valve is closed and the evacuation of the chamber is continued for a period of approximately 20 minutes. This procedure is repeated as many times as is necessary to remove essentially all of the ethylene oxide. At the conclusion of the fifth purge it is observed that the temperature of the catalyst bed has declined to a temperature of about 310 degrees F. and at that time, the electric coil is then reactivated to supply heat to the catalyst bed. The evacuation is repeated as many times as is necessary to thoroughly wash the sterilizer chamber of ethylene oxide and the sterilizer chamber is then ready to be opened for removal of sterilized items.

The oxidizer system of the invention can be supplied in different capacities for varied capacities of the sterilizer chamber. A number of sizes are provided to handle from 10 to 20 standard cubic feet per minute of evacuated sterilant gas mixtures from sterilizing chambers. In these units, the quantities of catalyst which are supplied range from 103 to 771 pounds, with the recycle-gas blowers sized to provide recycle gas flows of 900 to 1,800 standard cubic feet per minute.

The operating costs of these units compares very favorably to the operating costs for continuous-flow oxidizers which are representative of the prior art. The smallest of the these systems of the invention can be operated with an average operating cost of five cents per hour after initial preheating. In contrast, the continuous flow system of the prior art has an operating cost 10 times this amount for the same capacity of sterilizer. The economics are even more favorable for a larger oxidizer unit, which has as operating cost of ten cents per hour contrasted with eighty-four cents per hour for the operation of a continuous flow oxidizer capable of handling the same sized sterilizer.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims.

What is claimed is:

1. A batch method for the controlled oxidation of a combustible gas comprising the steps of:
   a. providing an oxidation housing having an entrance, an exit, and a predetermined quantity of solid catalyst in the presence of oxygen, said catalyst having a predetermined heat capacity;
   b. providing a closed containment space containing a volume of a preselected combustible gas;
   c. preheating said solid catalyst to a predetermined initiation temperature sufficient to initiate oxidation of said preselected combustible gas;
   d. transferring said preselected combustible gas from said closed containment space and into said entrance of said oxidation housing in contact with said solid catalyst and oxygen where oxidation of said combustible gas occurs and combustion products are produced;
   e. supplying ambient air to said entrance of said oxidation housing at essentially no more than a rate sufficient to maintain combustion of said preselected combustible gas, and independent of the temperature of both said solid catalyst and said combustible gas present within said entrance to said oxidation housing;
   f. discontinuing said preheating of said solid catalyst, said solid catalyst absorbing the heat exothermally released from the oxidation of said preselected combustible gas, and wherein the maximum temperature of said solid catalyst is limited to a safe temperature by the provision of a sufficient quantity of said solid catalyst to absorb the exothermal heat released from said oxidation without exceeding said safe temperature; and g. exhausting said combination products from said exit of said oxidation housing as exhaust gases.

2. The method of claim 1, further comprising the step of recirculating said exhaust gases from said exit of said oxidation housing back through said entrance of said oxidation housing continuously to minimize the energy needed for said preheating of said catalyst.

3. The method of claim 2, wherein the said preselected combustible gas is available in a concentration in excess of the concentration at which the catalyst can process, and said exhaust gases are recirculated through said oxidation housing at a rate preselected to provide a sufficient reduction in the concentration of said combustible gas within said entrance to said oxidation housing.

4. The method of claim 3, wherein transfer of said preselected combustible gas from said closed containment space is controlled to insure a reduced concentration of the combustible gas with respect to said recirculated air within said oxidation housing.

5. The method of claim 2, further comprising the steps of:
monitoring the concentration of said preselected combustible gas; and
adjusting the rate of circulation of said air recirculated through said oxidation housing to reduce the concentration of the combustible gas within said oxidation housing.

6. The method of claim 5 wherein said concentration is reduced below a preset maximum concentration.

7. The method of claim 2, wherein the rate of continuously recirculating said exhaust gases through said oxidation housing is controlled to control the time during which said combustible gas is in contact with said solid catalyst within said oxidation housing.

8. The method of claim 2, wherein the rate of continuously recirculating said exhaust gases through said oxidation housing is controlled to control the frictional heat energy imparted to said solid catalyst.

9. The method of claim 2, and further comprising the step of providing at least one other gas in said closed containment space forming a combustible gas mixture with said preselected combustible gas, and wherein a sufficient quantity of said predetermined quantity of solid catalyst is provided to limit the temperature of said solid catalyst to oxidize only said preselected combustible gas and not oxidize said at least one other gas.

10. The method of claim 9, wherein said at least one other gas becomes adsorbed onto said catalyst, and further comprising the step of purging said oxidation housing with air, after said exhausting step, to remove any of said at least one other gas which has become adsorbed onto said catalyst.

11. The method of claim 9 wherein said preselected combustible gas is present with at least one other gas at a concentration with respect to said combustible gas mixture of from 10 to 27 volume percent.

12. The method of claim 2, wherein said preheating step is performed when necessary to keep the temperature of said solid catalyst above said predetermined initiation temperature by heating said exhaust gases which are recirculated in said recirculating step, after leaving said exit of said oxidation housing and before returning to said entrance of said oxidation housing.

13. The method of claim 1, wherein said supplying of ambient air to said oxidation housing step is accomplished by reducing the pressure at said entrance to said oxidation housing and placing said entrance to said oxidation housing in communication with said ambient air to cause said ambient air to mix with said combustible mixture, as said ambient air is supplied to said entrance of said oxidation housing.

14. The method of claim 1, wherein said exhausting of said combustion products from said exit of said oxidation housing is physically and inherently limited to the flow rate of the combined volume of said ambient air and said preselected combustible gas introduced to said entrance of said oxidation housing.

15. The method of claim 1 wherein said preselected combustible gas from said closed containment space and into said entrance of said oxidation housing is performed by evacuating the combustible gas from said containment space and pumping said combustible gas into said oxidation housing.

16. The method of claim 15, further comprising the steps of:
introducing air into said closed containment space after the said combustible gas is evacuated from said containment space; and
evacuating said air introduced into said containment space and into said entrance of said oxidation housing is performed by evacuating the combustible gas from said closed containment space and pumping said combustible gas into said oxidation housing.

17. The method of claim 1, further comprising the step of raising the temperature of said catalyst to maintain the temperature of said catalyst above said initiation temperature.

18. The method of claim 1, wherein said closed containment space is within a sterilizer and wherein said combustible gas is ethylene oxide.

19. The method of claim 1 wherein said solid catalyst is $MnO_2$—$CuO$.

20. A system for the controlled oxidation of a finite volume of combustible gas comprising:
a. oxidation housing having an entrance, an exit, and a predetermined quantity of solid catalyst in the presence of oxygen, said catalyst having a predetermined heat capacity;
b. a sterilizer having a closed containment space;
c. a preheater having an outlet and an inlet, and connected in series with said entrance and said exit, respectively of said oxidation housing;
d. a gas blower having an outlet and an inlet, and connected in series with said preheater and said oxidation housing;
e. a vacuum pump having an outlet in communication with said entrance of said oxidation housing, and an inlet in communication with said containment space of said sterilizer;
f. a conduit having an inlet in communication with said exit of said oxidation housing, and an outlet in communication with the atmosphere, to provide an extended path for combusted gasses exiting said oxidation housing.

21. The system of claim 20 further comprising:
a valve connected in series between said inlet of said gas blower and said exit of said oxidation chamber.

* * * * *